(12) United States Patent
Frey et al.

(10) Patent No.: US 8,524,938 B2
(45) Date of Patent: *Sep. 3, 2013

(54) PROCESS FOR LIGHTENING THE COLOR OF POLYOL ESTERS

(75) Inventors: Guido D. Frey, Riedstadt (DE); Thorsten Kreickmann, Oberhausen (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 346 days.

This patent is subject to a terminal disclaimer.

(21) Appl. No.: 12/924,830

(22) Filed: Oct. 6, 2010

(65) Prior Publication Data

US 2011/0087046 A1 Apr. 14, 2011

(30) Foreign Application Priority Data

Oct. 8, 2009 (DE) .................. 10 2009 048 774

(51) Int. Cl.
*C07C 69/003* (2006.01)
(52) U.S. Cl.
USPC .............................. 560/98; 560/248; 560/183
(58) Field of Classification Search
USPC .............................. 560/183, 98, 248; 528/271
See application file for complete search history.

(56) References Cited

U.S. PATENT DOCUMENTS

| | | | | |
|---|---|---|---|---|
| 2,469,446 A | | 5/1949 | Strauss | 260/410.6 |
| 2,628,249 A | | 2/1953 | Bruno, Jr. | 260/475 |
| 3,031,400 A | | 4/1962 | Dobson et al. | 260/475 |
| 5,142,071 A | * | 8/1992 | Kluesener et al. | 554/172 |
| 5,318,790 A | * | 6/1994 | Houston et al. | 426/423 |
| 5,397,494 A | * | 3/1995 | Vega et al. | 510/536 |
| 6,423,856 B1 | * | 7/2002 | Springer et al. | 554/173 |
| 6,939,980 B2 | * | 9/2005 | Memita et al. | 554/170 |
| 7,326,804 B2 | * | 2/2008 | Kim et al. | 560/129 |
| 8,158,816 B2 | * | 4/2012 | Frey et al. | 560/248 |
| 8,188,267 B2 | * | 5/2012 | Buchanan et al. | 536/119 |

FOREIGN PATENT DOCUMENTS

| | | |
|---|---|---|
| DE | 199 40 991 | 1/2001 |
| GB | 783463 | 9/1957 |
| GB | 813867 | 5/1959 |
| JP | 2002-047248 * | 2/2002 |
| WO | WO 94/18153 | 8/1994 |

OTHER PUBLICATIONS

Bried et al., "Synthetic Lubricant Fluids From Branched-Chain Diesters. Physical and Chemical Properties of Pure Diesters", Industrial and Engineering Chemistry, American Chemical Society, US, Bd. 39, Apr. 1, 1947, pp. 484-491.
EPO Search Report.
Ullmann's Encyclopaedia of Industrial Chemistry, 5th edition, 1985, VCH Verlagsgesellschaft, vol. A1, pp. 305-319; 1990, vol. A15, pp. 438-440.
Kirk Othmer, Encyclopaedia of Chemical Technology, 3rd edition, John Wiley & Sons, 1978, vol. 1, pp. 778-787; 1981, vol. 14, pp. 496-498.
Goldsmith, Polyhydric Alcohol Esters of Fatty Acids, Chem. Rev. 33, 257 ff. (1943).
Johnson (edit.), Fatty Acids in Industry (1989) Chapter 9, Polyoxyethylene Esters of Fatty Acids; and H. Suter, Phthalsäureanhydrid and seine Verwendung [Phthalic anhydride and use thereof], Dr. Dietrich Steinkopf Verlag, Darmstadt 1972.

* cited by examiner

*Primary Examiner* — Johann R Richter
*Assistant Examiner* — Pancham Bakshi
(74) *Attorney, Agent, or Firm* — Michael W. Ferrell

(57) ABSTRACT

The present invention relates to a process for lightening the color of polyol esters by reacting polyols with linear or branched aliphatic monocarboxylic acids having 3 to 20 carbon atoms, wherein the reaction product is worked up without using adsorbents and comprises a treatment with ozone or ozone-containing gases and an immediately subsequent steam treatment with subsequent drying.

33 Claims, No Drawings

PROCESS FOR LIGHTENING THE COLOR OF POLYOL ESTERS

CLAIM FOR PRIORITY

This application is based on German Application No. 10 2009 048 774.3, entitled "Verfahren zur Farbaufhellung von Polyolestern", filed Oct. 8, 2009, the priority of which is hereby claimed and the disclosure of which is incorporated herein by reference.

TECHNICAL FIELD

The invention relates to a process for lightening the color of polyol esters formed from linear or branched aliphatic monocarboxylic acids having 3 to 20 carbon atoms by treating the polyol ester with ozone or ozone-containing gases.

BACKGROUND OF INVENTION

Esters of polyhydric alcohols, also known as polyol esters, find a variety of uses on a large scale in industry, for example as plasticizers or lubricants. The selection of suitable starting materials allows the physical properties, for example boiling point or viscosity, to be controlled, and the chemical properties, such as hydrolysis resistance or stability to oxidative degradation, to be taken into account. Polyol esters can also be tailored to the solution of specific performance problems. Detailed overviews of the use of polyol esters can be found, for example, in Ullmann's Encyclopaedia of Industrial Chemistry, 5th edition, 1985, VCH Verlagsgesellschaft, Vol. A1, pages 305-319; 1990, Vol. A15, pages 438-440, or in Kirk Othmer, Encyclopaedia of Chemical Technology, 3rd edition, John Wiley & Sons, 1978, Vol. 1, pages 778-787; 1981, Vol. 14, pages 496-498.

The use of polyol esters as lubricants is of great industrial significance, and they are used particularly for those fields of use in which mineral oil-based lubricants meet the requirements made only incompletely. Polyol esters are used especially as turbine engine and instrument oils. Polyol esters for lubricant applications are based frequently on 1,3-propanediol, 1,3-butanediol, 1,4-butanediol, 1,2-hexanediol, 1,6-hexanediol, neopentyl glycol, trimethylolpropane, pentaerythritol, 2,2,4-trimethylpentane-1,3-diol, glycerol or 3(4),8(9)-dihydroxymethyltricyclo[5.2.1.0$^{2,6}$]decane, also known as TCD alcohol DM, as the alcohol component.

Polyol esters are also used to a considerable degree as plasticizers. Plasticizers find a variety of uses in plastics, coating materials, sealing materials and rubber articles. They interact physically with high molecular weight thermoplastic substances, without reacting chemically, preferably by virtue of their swelling and dissolution capacity. This forms a homogeneous system, the thermoplastic range of which is shifted to lower temperatures compared to the original polymers, one result being that the mechanical properties thereof are optimized, for example deformation capacity, elasticity and strength are increased, and hardness is reduced.

In order to open up the widest possible fields of use to plasticizers, they must fulfil a series of criteria. They should ideally be odorless, colorless, and light-, cold- and heat-resistant. Moreover, it is expected that they are insensitive to water, comparatively nonflammable and not very volatile, and are not harmful to health. Furthermore, the production of the plasticizers should be simple and, in order to meet ecological requirements, avoid waste substances, such as by-products which cannot be utilized further and wastewaters comprising pollutants.

A specific class of polyol esters (they are referred to as G esters for short) contains diols or ether diols as the alcohol component, for example ethylene glycol, diethylene glycol, triethylene glycol, tetraethylene glycol, 1,2-propylene glycol or higher propylene glycols. They can be prepared in different ways. In addition to the reaction of alcohol and acid, optionally in the presence of acidic catalysts, further processes are employed in practice to obtain G esters, including the reaction of diol with acid halide, the transesterification of a carboxylic ester with a diol, and the addition of ethylene oxide onto carboxylic acids (ethoxylation). In industrial manufacture, only the direct reaction of diol and carboxylic acid and the ethoxylation of carboxylic acids have become established as production processes, preference usually being given to the esterification of diol and acid. This is because this process can be performed with no particular complexity in conventional chemical apparatus, and it affords chemically homogeneous products. Compared to this, ethoxylation requires extensive and costly technical equipment. Ethylene oxide is a very reactive chemical substance. It can polymerize explosively and forms explosive mixtures with air within very wide mixing ranges. Ethylene oxide irritates the eyes and respiratory pathways, leads to chemical burns and to liver and kidney damage, and is carcinogenic. The handling thereof therefore entails extensive safety measures. Moreover, scrupulous cleanliness of storage apparatus and reaction apparatus has to be ensured, in order to rule out the formation of undesired impurities as a result of side reactions of the ethylene oxide with extraneous substances. Finally, the reaction with ethylene oxide is not very selective, since it leads to mixtures of compounds of different chain length.

The direct esterification of alcohols with carboxylic acids is one of the basic operations in organic chemistry. In order to increase the reaction rate, the conversion is typically performed in the presence of catalysts. The use of one of the reactants in excess and/or the removal of the water formed in the course of the reaction ensures that the equilibrium is shifted in accordance with the law of mass action to the side of the reaction product, i.e. of the ester, which means that high yields are achieved.

Comprehensive information regarding the preparation of esters of polyhydric alcohols, also including esters of ethylene glycols and fatty acids, and regarding the properties of selected representatives of these compound classes can be found in Goldsmith, Polyhydric Alcohol Esters of Fatty Acids, Chem. Rev. 33, 257 ff. (1943). For example, esters of diethylene glycol, of triethylene glycol and of polyethylene glycols are prepared at temperatures of 130 to 230° C. over reaction times of 2.5 to 8 hours. To remove the water of reaction, carbon dioxide is used. Suitable catalysts mentioned for the esterification of polyhydric alcohols are inorganic acids, acidic salts, organic sulphonic acids, acetyl chloride, metals or amphoteric metal oxides. The water of reaction is removed with the aid of an entraining agent, for example toluene or xylene, or by introducing inert gases such as carbon dioxide or nitrogen.

The production and the properties of fatty acid esters of the polyethylene glycols are discussed by Johnson (edit.), Fatty Acids in Industry (1989) Chapter 9, Polyoxyethylene Esters of Fatty Acids, and a series of preparative details are given. Higher diester concentrations are achieved by the increase in the molar ratio of carboxylic acid to glycol. Suitable measures for removing the water of reaction are azeotropic distillation in the presence of a water-immiscible solvent, heating while passing through an inert gas, or performing the reaction under reduced pressure in the presence of a desiccant. When the addition of catalysts is dispensed with, longer reaction times and higher reaction temperatures are required. Both reaction conditions can be made milder by the use of catalysts. In addition to sulphuric acid, organic acids such as p-toluenesulphonic acid and cation exchangers of the polystyrene type are the preferred catalysts. The use of metal powders, such as tin or iron, is also described. According to the teaching from U.S. Pat. No. 2,628,249, color problems in the case of catalysis with sulphuric acid or sulphonic acids can be alleviated when working in the presence of activated carbon.

One procedure in which esters of diethylene glycol and of triethylene glycol and of caprylic acid are prepared without addition of catalyst is known from U.S. Pat. No. 2,469,446. The esterification temperature is in the range from 270 to 275° C. and the water of reaction is driven out by means of a carbon dioxide stream.

In the reaction regime in which the addition of a catalyst is dispensed with, a molar excess of the particular carboxylic acid is generally employed, which, owing to its acidity, also acts as a catalyst.

For the removal of the water of reaction formed in the formation of ester from the polyol and the carboxylic acids, various processes are known. For example, the water of reaction formed is distilled out of the reaction vessel together with the excess carboxylic acid and passed into a downstream phase separator in which carboxylic acid and water separate according to their solubility properties. In some cases, the carboxylic acid used also forms an azeotrope with water under the reaction conditions, and is capable of removing the water of reaction as an entraining agent. Other methods employed include azeotropic distillation in the presence of an added water-immiscible solvent, heating of the reaction mixture while passing through an inert gas, the reaction of the polyol and carboxylic acid starting materials under reduced pressure or in the presence of a desiccant. Especially the removal of water by azeotropic distillation has been found to be useful for the establishment of the equilibrium in the preparation of polyol esters. According to the procedure known from DE 199 40 991 A1, the water-immiscible solvent which acts as an entraining agent and must have a boiling point of less than 112° C. is added to the reaction mixture only on attainment of a temperature of at least 140° C.

In the industrial process, the mixture of water and carboxylic acid removed is separated in a phase separator into the organic and aqueous phases, the aqueous phase is discharged and the carboxylic acid is recycled back into the esterification reaction. For the workup of the crude ester, for example, U.S. Pat. No. 5,324,853 A1 proposes removing excess carboxylic acid by means of passage of nitrogen or steam, adding an adsorbent, neutralizing residual organic acid with a base, and filtering off solids obtained. The residual amounts of acid present in the filtrate are removed with the passage of steam or nitrogen with simultaneous application of a reduced pressure and recycled back into the esterification reaction. Solids obtained in the vacuum treatment are removed in a final fine filtration. One task of the adsorbent added, for example activated carbon, is to improve the color of the polyol ester.

According to the procedure known from U.S. Pat. No. 2,469,446 A1, the crude ester obtained after removal of the water of reaction and of excess, unconverted starting materials, for example carboxylic acid, is first treated with an alkaline reagent, for example with an aqueous sodium carbonate or sodium hydroxide solution, in order to remove last residues of acidic constituents. After washing with water, and treatment with bleaching earth and activated carbon, the last traces of odorous substances can be removed by applying reduced pressure at elevated temperature. In some cases, the treatment with bleaching agents and activated carbon has to be repeated more than once in order to produce polyol esters with satisfactory color properties.

Measures for improving the color of crude esters, such as oxidation, for example with hydrogen peroxide, or the adsorption of activated carbon, are known from the general prior art, for example from H. Suter, Phthalsäureanhydrid and seine Verwendung [Phthalic anhydride and use thereof], Dr. Dietrich Steinkopf Verlag, Darmstadt 1972. To improve the color of ester compounds based on polyols, WO 94/18153 A1 proposes a subsequent treatment with an aqueous hydrogen peroxide solution.

In addition, the prior art also discusses the action of ozone or ozone-containing gases on esters for color lightening. According to GB 783,463, esters of dicarboxylic acids, especially those based on oxo alcohols, are treated with ozone-containing air or ozone-containing oxygen below 100° C. This is followed by washing with an aqueous alkali metal hydroxide solution and then washing with water. This is followed by drying, for example by adding a desiccant or by heating under reduced pressure and subsequent filtration. The process steps otherwise customary in the workup of crude ester mixtures, such as treatment with activated carbon as an adsorbent or steam treatment to remove residual alcohol traces, may also follow the ozone treatment. According to the teaching of GB 813,867, the action of ozone is followed by treatment with a reducing agent, for example by washing with an aqueous solution comprising an alkali metal sulphite or by hydrogenation over a metal catalyst. There follow the process steps customary for the workup of crude esters. The measure of treatment with a reducing agent allows the peroxide content in the ester to be lower. According to U.S. Pat. No. 3,031,491 A1 too, the ozone treatment is followed by contacting of the crude esters with a reducing agent, which can reduce the peroxide content in the crude ester. According to the teaching of DE 27 29 627 A1, the ozone treatment is performed on carboxylic esters at a temperature of 15 to 90° C. with ozonized air, the ozone concentration being adjusted to a content of 5 to 50 mg/l. The ozone treatment is then followed by neutralization with an aqueous alkali metal hydroxide solution and washing with water. The action of direct steam under reduced pressure removes volatile alcohol and water traces. Subsequently, the product is contacted with an adsorbent and finally filtered.

Owing to the quality criteria described at the outset for polyol esters, the process steps in the esterification stage with removal of the water of reaction and in the workup of the crude ester are very important process features, since the adjustment of these process steps influences the sensory and optical properties of the end products to a significant degree. More particularly, high demands are placed on the color properties, such as low color number and high color stability, of the polyol esters. The structure of the starting materials, of the polyhydric alcohols and of the acids, is, in contrast, crucial for the mechanical and thermal properties of the polymer materials plasticized with the polyol esters and influences the hydrolysis and oxidation stability of lubricants.

The treatment with an adsorbent, for example activated carbon, high-surface area polysilicic acids, such as silica gels (silica xerogels), kieselguhr, high-surface area aluminium oxides and aluminium oxide hydrates, or mineral materials such as clays or carbonates, during the workup of the crude polyol ester to improve the color is a conventional process, but it requires additional filtration steps which mean a considerable level of complexity in a process performed industrially. Valuable product likewise remains adhering in the filter device and on the adsorbent, such that valuable product is lost in an additional filtration step.

Treatment with oxidizing agents, such as with hydrogen peroxide, ozone or with ozone-containing gases to lighten the color can also be found to be problematic since it can result in formation of organic peroxides during the treatment of the polyol esters. Traces of peroxides reduce the ester quality and the performance properties of the plasticized polymer products and of the lubricants produced on the basis of polyol esters. Peroxide traces also impair the storage performance of the polyol esters, and an increase in the peroxide number is observed during storage in spite of exclusion of oxidizing agents such as air. To reduce the peroxide number, the prior art proposes an additional treatment with a reducing agent. Although this process is capable of reducing the peroxide number, such an operation means an additional working step in which the reducing agent has to be provided and removed again after use thereof.

SUMMARY OF INVENTION

It has now been found that, in the treatment of the crude polyol ester with ozone or ozone-containing gases, light-colored products can be arrived at without using adsorbents when a treatment with ozone or ozone-containing gases having an amount of 0.01 to 5.0 grams of ozone per liter of polyol ester is undertaken and immediately followed, without further intermediate steps, by a treatment with steam and final drying of the polyol ester, the conditions during the treatments, such as temperature, duration and pressure to be applied, being tailored to the particular polyol ester.

Surprisingly, in this procedure, a light-colored polyol ester is obtained, which has an exceptionally low peroxide number which remains stable and does not increase even over a prolonged storage period.

The invention therefore consists in a process for lightening the color of polyol esters by reacting polyols with linear or branched aliphatic monocarboxylic acids having 3 to 20 carbon atoms and then working up the reaction mixture without the use of adsorbents. The process is characterized in that removal of unconverted starting compounds is followed by treating the reaction product with ozone or ozone-containing gases in an amount of 0.01 to 5.0 grams of ozone per liter of polyol ester, immediately thereafter performing a steam treatment without further intermediate steps and drying the remaining polyol ester.

The novel procedure is notable for great reliability not only in laboratory and test operation, but in particular also in industrial plants. Even in continuous form, it is easy to perform and affords polyol esters with high purity. The treatment of the crude ester with ozone or ozone-containing gases with immediately subsequent steam treatment and further drying leads to excellent color properties and remarkable color stability of polyol esters, which additionally have only a low peroxide number. The peroxide number also remains stable at a low level over a prolonged storage time.

Further features and advantages will become apparent from the discussion which follows.

DETAILED DESCRIPTION

In connection with the treatment of the crude ester obtained after removal of unconverted starting compounds with ozone or ozone-containing gases, ozone is used in an amount of 0.01 to 5.0 grams, preferably 0.2 to 0.8 gram, per liter of polyol ester. Higher amounts of ozone are not advisable owing to increased onset of degradation reactions of the polyol ester skeleton. In addition to the reduction in the polyol ester content determined by gas chromatography, in the case of an excessively high ozone input, a rise is also observed in the acid or neutralization number, for example determined according to DIN EN ISO 3682/ASTM D 1613, as is an increase in the peroxide number, expressed in milliequivalents of oxygen per kilogram of polyester and, for example, determined according to ASTM E 298. The course of these indices can be interpreted by an increased onset of acid formation when too high an amount of ozone is used. In the case of excessively low ozone inputs, the advantageous influence on the lightening of color is too small, or disproportionately long treatment times have to be accepted.

Ozone is used either in pure form or in a mixture with gases, for example with air or oxygen, or in a mixture with inert gases, such as with nitrogen, with carbon dioxide or with the noble gases, such as helium or argon. When ozone-containing gases are used for the treatment, the ozone concentration is appropriately 2 to 200, preferably 10 to 100, grams of ozone per $m^3$ of gas mixture. Preference is given to working with a mixture of ozone in oxygen.

For the preparation of ozone or ozone-containing gas mixtures, commercially available ozone generators are available, for example instruments designated Ozone Systems SMO series, PDO series, SMA series or PDA series from ITT Wedeco GmbH.

The treatment with ozone or ozone-containing gases can be effected over a wide temperature range. The lower temperature limit is determined by the viscosity and crystallization properties of the reaction medium, which should still be sufficiently pumpable even at low temperatures. At excessively high temperatures, an increased onset of decomposition of the ozone has to be expected. For example, it is possible to work over a temperature range from −30° C. up to a temperature of 130° C. Preference is given to employing temperatures of 20 to 100° C. and especially of 30 to 80° C. The duration of treatment with ozone can likewise extend over a wide range; the oxidizing agent is typically employed over a few minutes up to several hours, for example from one minute up to three hours, preferably of 20 to 90 minutes. Higher temperatures and longer treatment times should be avoided owing to an increased occurrence of decomposition of the ozone and also of the polyol ester. Based on the treatment time, the ozone input should be 0.1 to 5.0, preferably 0.2 to 0.9, grams of ozone per hour and liter of polyol ester.

The particular conditions of the treatment with ozone or ozone-containing gases should be tailored to the particular polyol ester in order to achieve optimal decolorization on the one hand, but as far as possible to prevent degradation reactions of the polyol ester on the other hand. Especially in the case of polyol esters based on ether diols, for example triethylene glycol or tetraethylene glycol, increased degradation of the ether structure can set in when the conditions in the treatment with ozone or ozone-containing gases, such as temperature, action time or ozone input, are not adjusted precisely to the particular polyol ester.

After the oxidative treatment, the crude ester, without further intermediate steps, is subjected immediately thereafter to a treatment with steam, which can be effected, for example, in a simple form by introducing steam into the crude product. One advantage of steam treatment is that ozone traces still present and traces of organic peroxides formed are destroyed in the course thereof and residues of the starting compounds are removed with the steam. Relatively large amounts of water still present are also driven out by the steam treatment. At the same time, this measure improves the color number and the color stability of the crude ester.

The steam treatment is generally performed at standard pressure, although the employment of a slightly reduced pressure, appropriately down to 400 hPa, is not ruled out. The steam treatment is generally performed at temperatures of 100 to 250° C., preferably of 150 to 220° C. and especially of 170 to 200° C., and is also guided by the physical properties of the polyol esters to be prepared in each case.

In the process step of steam treatment, it is found to be appropriate to proceed in a very gentle manner during the heating period until the attainment of the working temperature, in order to heat the crude ester treated with ozone to the required temperature for the steam treatment.

The duration of the steam treatment can be determined by routine tests and it is generally performed over a period of 0.5 to 5 hours. Too long a steam treatment leads to an undesired increase in the color number of the polyol ester and should therefore be avoided. An increased degradation reaction of the polyol ester to acidic compounds is also observed, the content of which is manifested in a rise in the neutralization number or acid number, for example determined according to DIN EN ISO 3682/ASTM D 1613. In the case of too short a treatment time, the destruction of ozone residues and traces of organic peroxides formed is incomplete, and the desired polyol ester still has too high an undesired peroxide number, expressed in milliequivalents of oxygen per kilogram of product and determined according to ASTM E 298. Another observation in the case of too short a treatment time is only a minor advantageous effect on the color number of the polyol ester.

As in the case of the treatment with ozone or ozone-containing gases, the conditions in the immediately subsequent steam treatment, such as temperature, pressure and duration, also have to be adjusted precisely to the particular polyol ester, in order to achieve an optimal result in relation to the color number of the polyol ester and in order to minimize residual contents of starting compounds, water and of peroxide traces as far as possible, and simultaneously to suppress degradation reactions. Especially in the case of polyol esters based on ether diols, for example triethylene glycol or tetraethylene glycol, the conditions in the steam treatment have to be tailored exactly to the particular polyol ester, in order to suppress the undesired degradation of the ether chain.

Remarkably, the steam distillate which has been removed from the desired polyol ester and is obtained after condensation of the steam removed from the reaction section has a comparatively high peroxide number. On the industrial scale, the occurrence of large amounts of steam and steam distillate with a high peroxide number can be found to be problematic for safety reasons, since organic and possibly inorganic peroxides can become concentrated in the attached columns and distillate receivers. It has been found to be appropriate to contact the removed steam laden with water and unconverted starting compounds, in which peroxides are also present, with noble metals of groups 9 to 11 of the periodic table of the elements (according to IUPAC recommendation 1985), for example with palladium or platinum. This measure can destroy the peroxide compounds present in the steam. The contacting is effected in gaseous form at the temperature of the steam removed in the presence of the noble metals, by, for example, passing the steam over a commercial noble metal catalyst in fixed bed form, which may either be supported or unsupported. For example, in a column section attached to the reactor section, solid internals can be installed, which have a woven or porous structure, for example a rectangular, honeycomb, round or other customary structure, to which the noble metals have been applied and through whose channels the gaseous and laden steam which has been passed through the crude ester and now removed passes. When the noble metal has been applied to a support, suitable supports are those customary for noble metal catalysts in industry, such as silicon dioxide, aluminium oxide, activated carbon, titanium dioxide or zirconium dioxide in their different manifestations.

It is also possible to provide solid arrangements composed of noble metals, for example fabrics, meshes, braids, wires, coils or sponges, in the column section in order to destroy peroxide compounds driven out with the steam.

It is also possible to treat the condensed liquid distillate removed, in which peroxides may be enriched, with noble metals of groups 9 to 11 of the periodic table of the elements to destroy peroxide compounds still present, for example at autogenous temperature with commercial supported or unsupported noble metal catalysts which may be used in fixed bed form or in suspension. It is also possible to contact a customary solid arrangement of noble metals, for example a fabric, a braid or wires, for example a platinum mesh, with the liquid distillate removed.

The steam treatment is followed by the drying of the polyol ester, for example by passing an inert gas through the product at elevated temperature. It is also possible simultaneously to apply a reduced pressure at elevated temperature and optionally to pass an inert gas through the product. Even without the action of an inert gas, it is possible to work only at elevated temperature or only under reduced pressure. The particular drying conditions, such as temperature, pressure and time, can be determined by simple preliminary tests and should be tailored to the particular polyol ester. In general, the working temperatures are in the range from 80 to 250° C., preferably 100 to 180° C., and the working pressures are from 0.2 to 500 hPa, preferably 1 to 200 hPa, and especially 1 to 20 hPa. After drying has ended, a light-colored polyol ester is obtained as the residue, without a filtration step being required, in order to obtain on-spec product. In a few exceptional cases, a filtration step may be required after the steam treatment or after the drying when, for example, solid catalyst residues are not completely removed after the esterification reaction has ended and after unconverted starting compounds have been removed, and hence before the workup of the reaction mixture. In a particular configuration of the process according to the invention, the drying of the remaining polyol ester immediately follows the steam treatment without further intermediate steps.

The reaction of polyols and aliphatic monocarboxylic acids can be performed without use of a catalyst. This variant of the reaction has the advantage that addition of extraneous substances, which can lead to undesired contamination of the polyol ester, to the reaction mixture is avoided. However, it is then generally necessary to maintain higher reaction temperatures because only in this way is it ensured that the reaction proceeds with a sufficient, i.e. economically acceptable, rate. It should be noted in this context that the rise in the temperature can lead to thermal damage to the polyol ester. It is therefore not always possible to avoid the use of a catalyst which facilitates the reaction and increases the reaction rate. Frequently, the catalyst may be an excess of the aliphatic monocarboxylic acid, which is simultaneously a reaction component of the polyol, such that the reaction proceeds autocatalytically. Otherwise, the customary esterification catalysts are suitable for influencing the reaction rate, such as sulphuric acid, formic acid, polyphosphoric acid, methanesulphonic acid or p-toluenesulphonic acid, and equally combinations of such acids. It is likewise possible to use metallic catalysts, such as titanium-, zirconium- or tin-containing catalysts, for example the corresponding alkoxides or carboxylates. It is also possible to use catalytically active compounds which are insoluble in the reaction system and solid under reaction conditions, such as alkali metal or alkaline earth metal hydrogensulphates, for example sodium hydrogen-sulphate, although the use of solid catalysts is restricted to a few exceptional cases, since solid catalysts have to be filtered out of the reaction mixture after the esterification has ended. In some cases, an additional fine filtration is also required during the workup of the crude polyol ester, in order to remove last residues of the solid catalyst. The amount of the catalyst used may extend over a wide range. It is possible to use 0.001% by weight up to 5% by weight of catalyst, based on the reaction mixture. Since greater amounts of catalyst, however, give barely any advantages, the catalyst concentration is typically 0.001 to 1.0% and preferably 0.01 to 0.5% by weight, based in each case on the reaction mixture. Appropriately, it may be decided by preliminary tests for each individual case whether to work without catalyst at higher temperature or with catalyst at lower temperature.

The esterification can be undertaken with stoichiometric amounts of polyol and aliphatic monocarboxylic acid. Preference is given, however, to allowing the polyol to react with excess monocarboxylic acid without addition of a catalyst, such that the excess monocarboxylic acid itself acts as a catalyst. Excess monocarboxylic acid, which generally has a lower boiling point than the polyol used, can also be removed from the crude ester by distillation in a simple manner and a filtration step is dispensable owing to the avoidance of solid catalysts. The aliphatic monocarboxylic acid is used in a 10 to 50% molar and preferably 20 to 40% molar excess per mole of hydroxyl group to be esterified in the polyol.

The water of reaction formed is distilled out of the reaction vessel in the course of the reaction together with the excess monocarboxylic acid and passed into a downstream phase separator in which the monocarboxylic acid and water separate according to their solubility properties. The monocarboxylic acid used may also form an azeotrope with water under the reaction conditions and be capable of removing the water of reaction as an entraining agent. The progress of the reaction can be monitored by the water obtained. The water which separates out is removed from the process, while the monocarboxylic acid from the phase separator flows back into the reaction vessel. The addition of a further organic solvent, such as hexane, 1-hexene, cyclohexane, toluene, xylene or xylene isomer mixtures, which assumes the task of the azeotroping agent, is not ruled out, but restricted to a few exceptional cases. The azeotroping agent can be added as early as at the start of the esterification reaction or on attainment of relatively high temperatures. When the theoretical amount of water expected has been obtained or the hydroxyl number, for example determined according to DIN 53240, has fallen below a fixed value, the reaction is ended by allowing the reaction mixture to cool.

The reaction between polyol and aliphatic monocarboxylic acid, depending on the starting materials, sets in within the range from about 120 to 180° C. and can be conducted to completion in different ways.

One configuration of the process according to the invention first involves heating proceeding from room temperature to a temperature up to a maximum of 280° C., preferably up to 250° C., and, with the temperature kept constant, lowering the pressure in stages proceeding from standard pressure, in order to facilitate the removal of the water of reaction. The selection of the pressure stages, whether one, two or more than two stages, and the pressure to be established at the particular stage may be varied over a wide range and adjusted to the particular conditions. For example, in a first stage, the pressure can be lowered proceeding from standard pressure first down to 600 hPa, and then the reaction can be conducted to completion at a pressure of 300 hPa. These pressure figures are guide values which are appropriately complied with.

In addition to the variation of the pressure, it is likewise also possible to alter the temperature proceeding from room temperature in one, two or more than two stages during the esterification reaction, such that, at constant pressure, the temperature is increased from stage to stage, typically up to a maximum temperature of 280° C. However, it has been found to be appropriate to heat to a maximum of 280° C. with the temperature rising from stage to stage, and also to lower the pressure from stage to stage. For example, the esterification reaction can be conducted proceeding from room temperature in a first stage at a temperature up to 190° C. A reduced pressure down to 600 hPa is likewise applied, in order to accelerate the driving-out of the water of reaction. On attainment of the temperature stage of 190° C., the pressure is lowered once again down to 300 hPa, and the esterification reaction is conducted to completion at a temperature up to 250° C. These temperature and pressure figures are guide values which are appropriately complied with. The temperature and pressure conditions to be established at the particular stages, the number of stages and the particular temperature increase or pressure reduction rate per unit time can be varied over a wide range and adjusted in accordance with the physical properties of the starting compounds and of the reaction products, the temperature and pressure conditions of the first stage being established proceeding from standard pressure and room temperature. It has been found to be particularly appropriate to increase the temperature in two stages and to lower the pressure in two stages.

The lower limit of the pressure to be established depends on the physical properties, such as boiling points and vapor pressures, of the starting compounds and of the reaction products formed, and is also determined by the plant apparatus. Proceeding from standard pressure, it is possible to work in stages within these limits, with pressures decreasing from stage to stage. The upper temperature limit, typically 280° C., should be complied with in order to prevent the formation of decomposition products, which adversely affect color among other properties. The lower limit of the temperature stages is determined by the reaction rate, which must still be sufficiently high to complete the esterification reaction within an acceptable time. Within these limits, it is possible to work in stages with temperatures rising from stage to stage.

The reaction mixture obtained after the reaction has ended comprises, as well as the polyol ester as the desired reaction product, possibly unconverted starting materials, especially aliphatic monocarboxylic acid still in excess, if an acid excess has been employed in accordance with the preferred configuration of the process according to the invention. For workup, excess and unconverted starting materials are distilled off, appropriately with application of a reduced pressure. In order to remove acidic catalysts, such as dissolved sulphuric acid or solid potassium hydrogensulphate, if added in the esterification stage, and in order to remove last residues of acidic constituents, it is also possible to provide a treatment with an alkaline reagent, for example with an aqueous sodium carbonate or sodium hydroxide solution, or, in exceptional cases, a filtration.

Thereafter, the crude ester freed of the unconverted starting compounds and any catalyst present is worked up according to the inventive measure comprising treatment with ozone or ozone-containing gases, immediately subsequent steam treatment and final drying, dispensing with the use of customary adsorbents, such as activated carbon, high-surface area polysilicic acids such as silica gels (silica xerogels), kieselguhr, high-surface area aluminium oxides and aluminium oxide hydrates, or mineral materials such as clays or carbonates, during the workup. Without the use of these auxiliaries, light-colored polyol esters with a sufficiently low peroxide number are obtained, which also satisfy the remaining specifications, such as water content, residual acid content and residual content of monoester.

The purified polyol ester remains, during the drying, as a residue in the reaction vessel with outstanding quality, and an additional filtration step is generally not required and is restricted only to a few exceptional cases.

The polyhydric alcohols or polyols used as starting materials for the process according to the invention satisfy the general formula (I)

$$R(OH)_n \qquad (I)$$

in which R is an aliphatic or cycloaliphatic hydrocarbon radical having 2 to 20 and preferably 2 to 10 carbon atoms, and n is an integer of 2 to 8, preferably 2, 3, 4, 5 or 6.

Suitable polyols are likewise compounds of the general formula (II)

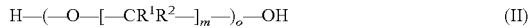
$$H\text{—}(\text{—}O\text{—}[\text{—}CR^1R^2\text{—}]_m\text{—})_o\text{—}OH \qquad (II)$$

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer of 1 to 10, preferably 1 to 8 and especially 1, 2, 3 or 4, o is an integer of 2 to 15, preferably 2 to 8 and especially 2, 3, 4 or 5.

Suitable polyols which can be converted by the process according to the invention to light-colored polyol esters are, for example, 1,3-propanediol, 1,3-butanediol, 1,4-butanediol, neopentyl glycol, 2,2-dimethylolbutane, trimethylolethane, trimethylolpropane, ditrimethylolpropane, trimethylolbutane, 2,2,4-trimethylpentane-1,3-diol, 1,2-hexanediol, 1,6-hexanediol, pentaerythritol or dipentaerythritol or 3(4),8(9)-dihydroxymethyltricyclo[5.2.1.0$^{2,6}$]decane.

Useful further polyols include ethylene glycol and 1,2-propylene glycol, and the oligomers thereof, especially the ether diols di-, tri- and tetraethylene glycol or dipropylene glycol, tripropylene glycol or tetrapropylene glycol. Ethylene and propylene glycols are industrially produced chemicals. The base substance for preparation thereof is ethylene oxide and propylene oxide, from which 1,2-ethylene glycol and 1,2-propylene glycol are obtained by heating with water under pressure. Diethylene glycol is obtained by ethoxylation from ethylene glycol. Triethylene glycol is obtained, like tetraethylene glycol, as a by-product in the hydrolysis of ethylene oxide to prepare ethylene glycol. Both compounds can also be synthesized by reacting ethylene glycol with ethylene oxide. Dipropylene glycol, tripropylene glycol, tetrapropylene glycol and higher propoxylation products are obtainable from the multiple addition of propylene oxide onto 1,2-propylene glycol.

To obtain light-colored polyol esters by the process according to the invention, linear or branched, aliphatic monocarboxylic acids having 3 to 20 carbon atoms in the molecule are used. Even though preference is given to saturated acids in many cases, depending on the particular field of use of the plasticizers or lubricants, it is also possible to use unsaturated carboxylic acids as a reaction component for ester synthesis. Examples of monocarboxylic acids as components of polyol esters are propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, cyclohexane-carboxylic acid, 2-ethylhexanoic acid, n-nonanoic acid, 2-methyloctanoic acid, isononanoic acid, 3,5,5-trimethylhexanoic acid, 2-propylheptanoic acid, 2-methylundecanoic acid, isoundecanecarboxylic acid, tricyclodecanecarboxylic acid and isotridecanecarboxylic acid. The novel process has been found to be particularly useful for the preparation of polyol esters of monoethylene glycol, or of the oligomeric ethylene glycols and of 1,2-propylene glycol, or of the oligomeric propylene glycols with $C_4$- to $C_{13}$- or $C_5$- to $C_{10}$-monocarboxylic acids, and for preparation of polyol esters based on 1,3-butanediol, neopentyl glycol, 2,2,4-trimethylpentane-1,3-diol, trimethylolpropane, ditrimethylolpropane, pentaerythritol or 3(4),8(9)-dihydroxymethyltricyclo[5.2.1.0$^{2,6}$]decane.

The polyol esters of ethylene glycol and the oligomers thereof are outstandingly suitable as plasticizers for all common high molecular weight thermoplastic substances. They have been found to be particularly useful as an additive to polyvinyl butyral which is used admixed with glycol esters as an intermediate layer for production of multilayer or composite glasses. They can likewise be used as coalescence agents or film-forming assistants in aqueous dispersions of polymers which find various uses as coating materials. The preparation process according to the invention makes it possible to prepare, in a simple manner, without the use of customary adsorbents, polyol esters with outstanding color properties which also satisfy further quality demands, such as low odor or a low acid number. The process according to the invention is particularly suitable for preparing triethylene glycol di-2-ethylhexanoate (3G8 Ester), tetraethylene glycol di-n-heptanoate (4G7 Ester), triethylene glycol di-2-ethylbutyrate (3G6 Ester), triethylene glycol di-n-heptanoate (3G7 Ester) or tetraethylene glycol di-2-ethylhexanoate (4G8 Ester).

The process according to the invention can be performed continuously or batchwise in the reaction apparatus typical for chemical technology. Useful apparatus has been found to be stirred tanks or reaction tubes which are provided with a feed line for ozone or ozone-containing gases, for example with an immersed tube or a base frit, and which are equipped with a heating apparatus and an attached column section.

The process according to the invention is illustrated in detail in the examples which follow, but it is not restricted to the embodiment described.

WORKING EXAMPLES

For the tests for color lightening, crude triethylene glycol di-2-ethylhexanoate with a color number of 89 Hazen units was used, which was obtained by esterification of triethylene glycol with a 2.6 molar amount of 2-ethylhexanoic acid without catalyst and without addition of entraining agent. The content determined by gas chromatography (% by weight) of triethylene glycol di-2-ethylhexanoate was 97.4%, that of triethylene glycol mono-2-ethylhexanoate 1.4%, and the remainder to 100% was 1.2%.

The workup of the crude triethylene glycol di-2-ethylhexanoate was performed with in each case 1 liter of crude product in a heatable 2 liter four-neck flask which was equipped with stirrer, internal thermometer and feed line with a bead frit of pore size G3. In the Modular 8HC (BHT 964) ozone generator from ITT Wedeco GmbH, an ozone-containing oxygen stream with an ozone concentration of 21 grams of ozone per cubic meter of oxygen was generated, which was passed at a rate of 0.025 m$^3$/hour via the bead frit through the crude ester at a temperature of 70° C. over a period of 0.5 hour while stirring vigorously.

For the subsequent steam distillation, the ozone feed line was replaced by a distillation apparatus with a 1 liter receiver and the 2 liter four-neck flask was equipped with an immersed tube for passage of steam. In the distillation column was positioned a platinum mesh through which the peroxide-laden steam driven out was passed.

After performing the steam distillation under the conditions described below, the supply of steam was stopped and a reduced pressure was applied over the distillation apparatus for final drying. The residue obtained was a light-colored, on-spec polyol ester without the use of adsorbents and reducing agents.

Example 1

The steam distillation which immediately follows the ozone treatment was performed using a platinum mesh under the following conditions:

| | |
|---|---|
| Working temperature of the steam distillation | 180° C. |
| Treatment time | 1 hour |

Subsequently, the following drying conditions were established:

| | |
|---|---|
| Pressure | 10 hPa |
| Drying temperature | 140° C. |
| Drying time | 0.5 h |

On completion of the workup, a light-colored polyol ester was obtained with the following contents determined by gas chromatography:

| | |
|---|---|
| Triethylene glycol di-2-ethylhexanoate content | 97.5% by weight |
| Triethylene glycol mono-2-ethylhexanoate content | 1.0% by weight |
| Remainder | 1.5% by weight | and the following indices:

| | |
|---|---|
| Hazen color number (DIN ISO 6271) | 16 |
| Neutralization number (mg KOH/g, DIN EN ISO 3682/ASTM D 1613) | 0.06 |
| Water content (% by weight, DIN 51777 Part 1) | 0.03 |
| Peroxide content (meq O/kg, ASTM E 298) | 1.35 |

In the distillate of the steam distillation, a peroxide content of 0.7 meq O/kg was found.

Example 2

Example 2 was carried out according to Example 1 with the sole exception that the steam distillation was effected without the use of a platinum mesh. The distillate obtained had a peroxide content of 9.0 meq O/kg. The indices of the purified polyol ester corresponded to the values displayed according to Example 1.

Example 3

Comparative Example

As a comparison, 1 liter of crude ester was sparged with pure oxygen at a temperature of 70° C. over a period of 0.5 hour. Only a slightly improved color number was observed in relation to the starting material, and the workup by means of steam distillation and subsequent drying was dispensed with. Only in the case of treatment times of up to 6 hours was a crude ester obtained with a Hazen color number of 45. Owing to the long treatment time, however, increased onset of cleavage reactions was observed, which led to a decrease in the diester content in the crude product to 97.1% by weight and to an increase in the monoester to 1.4% by weight, remainder 1.5% by weight (determined by gas chromatography).

The inventive measure of treating the crude esterification mixture with ozone after removing unconverted starting compounds, and immediately thereafter performing a steam treatment without further intermediate steps, produces light-colored polyol esters with high color stability without the use of adsorbents. In a further configuration of the process according to the invention, the steam driven out during the steam treatment can be contacted with a platinum mesh. This measure can significantly deplete the peroxide content in the distillate removed, which avoids safety problems which would have to be managed in the case of occurrence of amounts of distillate with a high peroxide content.

While the invention has been described in detail, modifications within the spirit and scope of the invention will be readily apparent to those of skill in the art. In view of the foregoing discussion, relevant knowledge in the art and references discussed above, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

The invention claimed is:

1. Process for lightening the color of polyol esters by reacting polyols with linear or branched aliphatic monocarboxylic acids having 3 to 20 carbon atoms and then working up the reaction mixture without the use of adsorbents, characterized in that removal of unconverted starting compounds is followed by treating the reaction product with ozone or ozone-containing gases in an amount of 0.01 to 5.0 grams of ozone per liter of polyol ester, immediately thereafter performing a steam treatment without further intermediate steps and drying the remaining polyol ester.

2. Process according to claim 1, characterized in that 0.2 to 0.8 gram of ozone per liter of polyol ester is used.

3. Process according to claim 1, characterized in that the ozone-containing gases used are gas mixtures of ozone with air, oxygen, nitrogen, carbon dioxide or a noble gas.

4. Process according to claim 3, characterized in that the reaction product is treated with an ozone containing gas wherein the ozone concentration is 2 to 200, grams of ozone per m$^3$ of gas mixture.

5. Process according to claim 1, characterized in that the treatment with ozone or ozone-containing gases is effected at temperatures of −30 to 130° C.

6. Process according to claim 1, characterized in that the ozone input is 0.1 to 5.0, grams of ozone per hour and liter of polyol ester.

7. Process according to claim 1, characterized in that the steam treatment is performed at a temperature of 100 to 250° C.

8. Process according to claim 1, characterized in that the steam removed in the steam treatment is contacted in gaseous form with noble metals of groups 9 to 11 of the periodic table of the elements.

9. Process according to claim 1, characterized in that the steam removed in the steam treatment is first condensed and the condensed liquid distillate is contacted with noble metals of groups 9 to 11 of the periodic table of the elements.

10. Process according to claim 8, characterized in that the noble metals of groups 9 to 11 of the periodic table of the elements are in fixed bed form.

11. Process according to claim 10, characterized in that the noble metals of groups 9 to 11 of the periodic table of the elements have been applied to a support.

12. Process according to claim 11, characterized in that the support used is silicon dioxide, aluminium oxide, activated carbon, titanium dioxide or zirconium dioxide.

13. Process according to claim 10, characterized in that the noble metals of groups 9 to 11 of the periodic table of the elements are arranged in the form of a fabric, mesh, braid, wire, coil or sponge.

14. Process according to claim 8, characterized in that the noble metals of groups 9 to 11 of the periodic table of the elements used are palladium or platinum.

15. Process according to claim 1, characterized in that the polyol ester is dried at temperatures of 80 to 250° C. and at pressures of 0.2 to 500 hPa.

16. Process according to claim 1, characterized in that the remaining polyol ester is dried immediately after the steam treatment without further intermediate steps.

17. Process according to claim 1, characterized in that the polyols used are compounds of the general formula (I)

$$R(OH)_n \tag{I}$$

in which R is an aliphatic or cycloaliphatic hydrocarbon radical having 2 to 20 and preferably 2 to 10 carbon atoms, and n is an integer of 2 to 8.

18. Process according to claim 1, characterized in that the polyols used are compounds of the general formula (II)

$$H\text{—}(\text{—}O\text{—}[\text{—}CR^1R^2\text{—}]_m\text{—})_o\text{—}OH \tag{II}$$

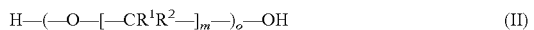

in which $R^1$ and $R^2$ are each independently hydrogen, an alkyl radical having 1 to 5 carbon atoms, or a hydroxyalkyl radical having 1 to 5 carbon atoms, m is an integer of 1 to 10, o is an integer of 2 to 15.

19. Process according to claim 17, characterized in that the polyols used are 1,2-propanediol, 1,3-propanediol, 1,3-butanediol, 1,4-butanediol, neopentyl glycol, 2,2-dimethylolbutane, trimethylolethane, trimethylolpropane, trimethylolbutane, 2,2,4-trimethylpentane-1,3-diol, 1,2-hexanediol, 1,6-hexanediol, pentaerythritol, ethylene glycol or 3(4),8(9)-dihydroxymethyltricyclo[5.2.1.0$^{2,6}$]decane.

20. Process according to claim 18, characterized in that the polyols used are ditrimethylolpropane, dipentaerythritol, diethylene glycol, triethylene glycol, tetraethylene glycol, dipropylene glycol, tripropylene glycol or tetrapropylene glycol.

21. Process according to claim 1, characterized in that the aliphatic monocarboxylic acid converted is propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, 2-ethylhexanoic acid, n-nonanoic acid, 2-methyloctanoic acid, isononanoic acid, 3,5,5-trimethylhexanoic acid or 2-propylheptanoic acid.

22. Process according to claim 1 for preparing triethylene glycol di-2-ethylhexanoate, tetraethylene glycol di-n-heptanoate, triethylene glycol di-2-ethylbutyrate or triethylene glycol di-n-heptanoate or tetraethylene glycol di-2-ethylhexanoate.

23. Process according to claim 4, characterized in that the ozone concentration in the gas mixture used to treat the reaction product is 10 to 100 grams of ozone per m$^3$ of gas.

24. Process according to claim 5, characterized in that the treatment with ozone or ozone-containing gases is effected at temperatures of 20 to 100° C.

25. Process according to claim 24, characterized in that the treatment with ozone or ozone-containing gases is effected at temperatures of 30 to 80° C.

26. Process according to claim 6, characterized in that the ozone input is 0.2 to 0.9 grams of ozone per hour and liter of polyol ester.

27. Process according to claim 7, characterized in that the steam treatment is performed at a temperature of 150 to 220° C.

28. Process according to claim 27, characterized in that the steam treatment is performed at a temperature of 170 to 200° C.

29. Process according to claim 15, characterized in that the polyol ester is dried at temperatures of 100 to 180° C. and at pressures of 1 to 200 hPa.

30. Process according to claim 29, characterized in that the polyol ester is dried at temperatures of 100 to 180° C. and at pressures of 1 to 20 hPa.

31. Process according to claim 17, characterized in that the polyols used are compounds of the general formula (I)

$$R(OH)_n \tag{I}$$

in which R is an aliphatic or cycloaliphatic hydrocarbon radical having 2 to 10 carbon atoms, and n is an integer of 2, 3, 4, 5 or 6.

32. Process according to claim 18, characterized in that the polyols used are compounds of the general formula (II)

$$H\text{—}(\text{—}O\text{—}[\text{—}CR^1R^2\text{—}]_m\text{—})_o\text{—}OH \tag{II}$$

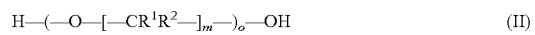

in which $R^1$ and $R^2$ are each independently hydrogen, methyl, ethyl or propyl, or the hydroxymethyl radical, m is an integer of 1 8, o is an integer of 2 to 8.

33. Process according to claim 32, characterized in that the polyols used are compounds of the general formula (II)

$$H\text{—}(\text{—}O\text{—}[\text{—}CR^1R^2\text{—}]_m\text{—})_o\text{—}OH \tag{II}$$

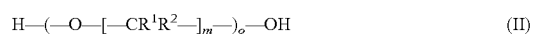

in which $R^1$ and $R^2$ are each independently hydrogen, methyl, ethyl or propyl, or the hydroxymethyl radical, m is an integer of 1, 2, 3 or 4, o is an integer of 2, 3, 4 or 5.

* * * * *